United States Patent [19]

French et al.

[11] 4,137,750

[45] * Feb. 6, 1979

[54] METHOD AND APPARATUS FOR ANALYZING TRACE COMPONENTS USING A GAS CURTAIN

[75] Inventors: John B. French; Neil M. Reid, both of Thornhill; Janette A. Buckley, Willowdale, all of Canada

[73] Assignee: The Governing Council of the University of Toronto, Toronto, Canada

[*] Notice: The portion of the term of this patent subsequent to May 17, 1994, has been disclaimed.

[21] Appl. No.: 790,214

[22] Filed: Apr. 25, 1977

Related U.S. Application Data

[63] Continuation-in-part of Ser. No. 555,202, Mar. 3, 1975, Pat. No. 4,023,398.

[51] Int. Cl.² ............................................ G01N 31/00
[52] U.S. Cl. .......................................... 73/23; 55/11; 55/102; 55/135; 55/270; 98/36; 250/281; 250/288
[58] Field of Search ................... 55/102, 11, 135, 269, 55/270, 2; 62/55.5; 98/36; 250/281, 288; 73/23

[56] References Cited

U.S. PATENT DOCUMENTS 4,023,398  5/1977  French et al. .................... 55/270

Primary Examiner—Bernard Nozick
Attorney, Agent, or Firm—Rogers, Bereskin & Parr

[57] ABSTRACT

Apparatus for analyzing trace components contained in a sample gas. The sample gas is directed into a reaction chamber and ionized. The resultant trace ions are drifted by an electric field, out of the sample gas, through an inert gas curtain and then through an orifice into a vacuum chamber where they are focused and analyzed. The curtain gas flow may be greater than the flow through the orifice, in which case the gas curtain acts as an ion window which is transparent to ions but blocks sample gas flow into the vacuum chamber. Alternatively, the curtain gas flow may be controlled to admit a desired flow of sample gas through the curtain into the vacuum chamber, in which case the gas curtain acts as a window for ions and as an infinitely variable orifice for the sample gas. Preferably the curtain gas is cryopumpable and is cryopumped by cooling the interior surface of the vaccum chamber.

13 Claims, 15 Drawing Figures

METHOD AND APPARATUS FOR ANALYZING TRACE COMPONENTS USING A GAS CURTAIN

This application is a continuation-in-part of our pending U.S. patent application Ser. No. 555,202 filed Mar. 3, 1975 now U.S. Pat. No. 4,023,398 entitled "Apparatus for Analyzing Trace Components."

This invention relates to methods and apparatus for analyzing trace components. More particularly, the invention relates to the analysis of trace components by ionizing the trace components, transferring the trace ions through a gas curtain into a vacuum, and analyzing the trace ions in the vacuum.

In the past, in the analysis of trace components in a sample gas, it has been known to ionize the trace components at atmospheric pressure, typically by chemical ionization. Typically an equilibrium level of ionization is created in the sample gas by exposing it to beta radiation from a radioactive source or by an electric discharge. After ionization, the sample gas (which consists of the trace components to be analyzed, in a carrier gas) is permitted to pass through an orifice into a vacuum chamber where the ions are focused and analyzed. In some prior art systems, an electric field is used to augment the flow of ions of one sign through the sample gas towards the orifice into the vacuum.

Various difficulties have existed in the prior art systems. One of the difficulties is that the source of the sample gas will often be the effluent from a gas chromatograph and will therefore have a fixed flow rate. The flow rate into the vacuum chamber is controlled by an aperture and must be matched to the flow rate of the gas chromatograph. If the aperture is too large, the pressure of the gas chromatograph effluent column will be pulled below atmospheric pressure, which is highly undesirable. If the aperture is too small (as is often the case when inadequate pumping is available), then a flow splitter or other separator must be used, usually causing loss of signal and other complications. The flow rate matching usually requires specific selection of the orifice size for each sample flow. The limitation of the orifice size restricts the ion signal into the vacuum chamber and severely limits the sensitivity of the system. In addition, when the sample gas source is changed (e.g. to a different gas chromatograph), the orifice size often must also be changed, which can be a slow and difficult process unless complicated mechanical aids are used.

Another difficulty in prior art systems is that the small orifices which must be used can easily become clogged with particulates which may be present in the sample gas. This reduces the reliability of the system and also (when the orifice is partly clogged) reduces its sensitivity. In addition, if the sample gas contains certain impurities, such as water vapour, unwanted clustering of the water vapour molecules can occur around the trace ions during the adiabatic expansion from the orifice into the vacuum chamber. This causes difficulty in interpreting the results of the analysis.

The present invention reduces these difficulties by transferring the trace ions through an inert curtain gas into the vacuum chamber under the influence of an electric field. In one embodiment of the invention, the gas curtain prevents the sample gas from entering the vacuum chamber and thereby prevents particulates and water vapour from entering the vacuum chamber. The curtain, however, is transparent to ions which are drifted through it by the electric field, and the curtain therefore acts as an ion window. If for example the sample gas used is the effluent from a gas chromatograph, the gas curtain eliminates the need to match the flow into the vacuum chamber to the gas chromatograph flow. This permits use of a single size orifice, the size of which is limited only by the available vacuum pumping speed. Preferably (as explained in our said copending application), but not necessarily, the gas of the gas curtain is cryopumpable and cryopumping is used, increasing the pumping speed and hence the permissible orifice size, and thus increasing the sensitivity of the system.

In another embodiment of the invention, the flow rate of the gas curtain is controlled so that some of the sample gas flow, as well as gas from the gas curtain, is permitted to enter the vacuum chamber. The gas curtain is in effect then pierced to a controlled extent by the sample gas. This also has various advantages, as will be explained.

Further objects and advantages of the invention will appear from the following description, taken together with the accompanying drawings, in which.

Figure 1A:
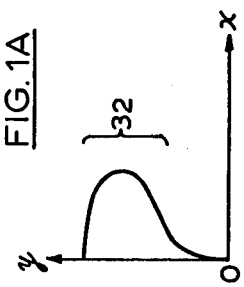
FIG. 1A is a graph of the ion creation region of the FIG. 1 apparatus.
Figure 1:
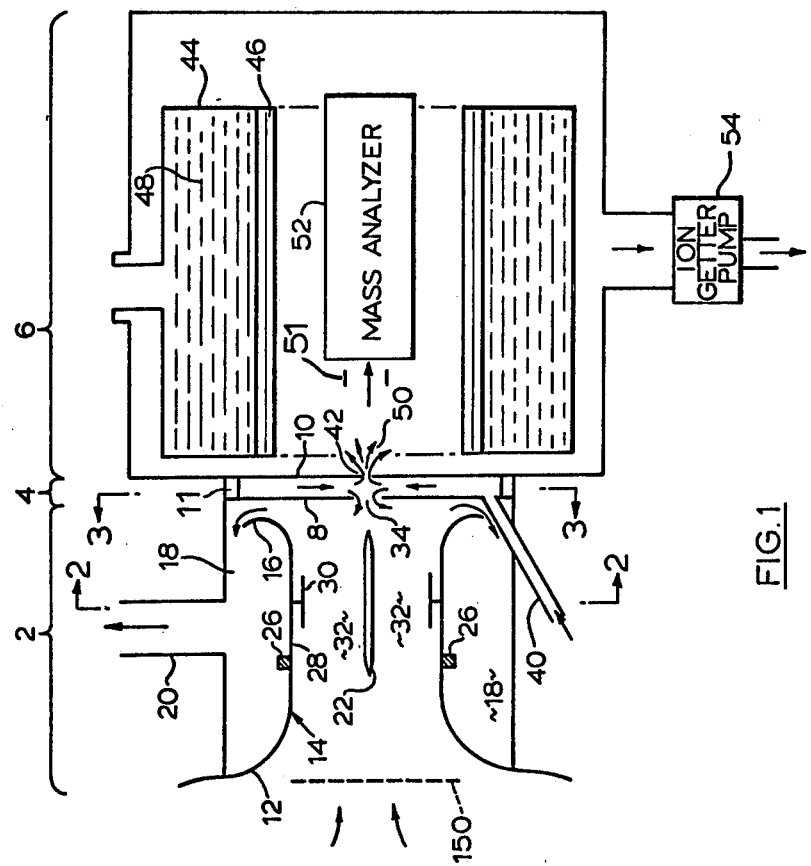
FIG. 1 is a diagrammatic view showing a first embodiment of the invention.
Figure 2:
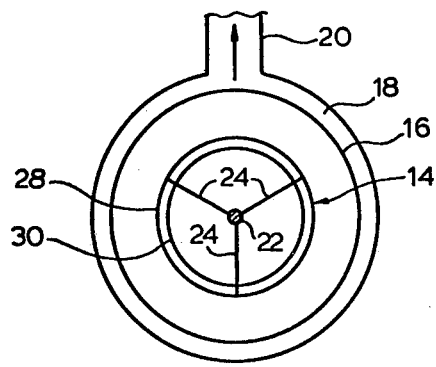
FIG. 2 is a sectional view along lines 2—2 of FIG. 1.

Reference is first made to FIGS. 1 and 2, which show one form of apparatus according to the invention. Such apparatus includes an ion reaction section generally indicated at 2, a gas curtain section 4, and a vacuum chamber (and analyzing) section 6. The reaction section 2 and the gas curtain section 4 are connected by an interface plate 8, while the gas curtain section 4 and the vacuum section 6 are in turn connected by an orifice plate 10. Plates 8, 10 are separated by an insulator 11.

The reaction section 2 includes a bellmouth inlet 12 and a cylindrical duct 14 connected at 16 to a plenum 18. The plenum 18 is connected by duct 20 to a synchronous fan (not shown) which operates to draw the air or other gas to be analyzed through the bellmouth inlet 12 and into the duct 14. Settling screens (not shown) may be provided in advance of the inlet 12 to eliminate vortices and to help provide laminar flow.

Located in the duct 14 is a central axially elongated electrode 22. The electrode 22 is supported in a position aligned with the axis of duct 14 by a triangular spider of insulating material such as nylon thread 24, as shown in FIG. 2. A separate insulated wire, not shown, is used to apply a desired voltage to the electrode 22. The portion of the duct 14 which surrounds the electrode 22 is insulated from the bellmouth 12 by an insulating joint diagrammatically indicated at 26, so that the wall portion of the duct 14 downstream of the joint 26 forms a second or outer electrode 28. Located between the two electrodes 22, 28 is ring-shaped ionizing device 30 such as a tritium foil.

In operation, air or other carrier gas containing the trace gas to be analyzed is drawn into the cylindrical duct 14 by the synchronous fan at a rate such as to provide a flow which is laminar but which is of sufficiently high velocity to minimize the effects of species diffusion. As the mixture passes the ionizing device foil 30, ion creation occurs in the region 32, forming a mixture of positive and negative ions in the gas. The ion creation region 32 is annular in form and its profile is shown in FIG. 1A, where distance from the foil is plotted along the Y axis (the foil being located at the origin) and the relative number of ions formed is plotted along the X axis.

During the ion creation, the beta rays from the tritium foil ionize components of the air or other carrier gas, resulting (after a series of reactions in the air or carrier gas) in the production of primary reactant ions. Some of the primary reactant ions then react with molecules of the trace gas to form product ions from the trace gas. This results in a mixture of product ions and reactant ions. From this mixture, the product ions are to be preferentially selected and analyzed.

An electric field, caused by appropriate potentials applied to the electrodes 22 and 28, the interface plate 8, and the orifice plate 10, is superimposed on the fluid flow. Ions are thus caused to drift with a local velocity $\vec{V}_1 = \vec{V}_f + K\vec{E}$, where $\vec{V}_f$ is the local fluid velocity, $\vec{E}$ is the local electric field vector and K is the mobility of the species in question. The potentials applied to the device, and the geometry of the device, are arranged (as will be explained in more detail presently) such that the desired ions of the selected polarity and any mobility are caused to converge in an approximately conical fashion from the reaction region 32 to a central region downstream of the front of the central electrode 22 and generally aligned with the axis of the electrode 22. The desired ions are thence carried forward in a concentrated flux toward a central aperture 34 in the interface plate 8. A portion of the ions originating from the sample flowing through the reaction region 32 passes through the central aperture 34 in the interface plate; typically a flux concentration factor of between sixty and one hundred may be achieved.

Figure 3:
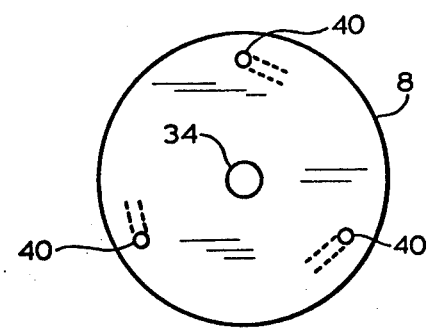
FIG. 3 is a sectional view along lines 3—3 of FIG. 1.

The transfer of the concentrated ions into the vacuum and analyzer section 6 will now be described. The transfer occurs through the gas curtain section 4. The gas curtain section 4 is supplied with an appropriate curtain gas (such as $CO_2$) which is selected to minimize reactions with the ions to be sampled and which preferably can be cryopumped in the vacuum section 6. The curtain gas, which acts as a curtain or gas membrane between the reaction section 2 and the vacuum section 6, is directed into the gas curtain section 4 by inlet ducts 40 (FIG. 3) arranged to create a generally circular flow pattern having a circumferential component but directed generally radially inwardly in the gas curtain section 4. The curtain gas is supplied at sufficient flow to match the ingestion into the vacuum section 6 and to provide a small excess which effuses gently out through the central hole 34 in the interface plate 8, at sufficient flow to prevent passage of the carrier gas into the space between the interface plate 8 and the orifice plate 10. However, the concentrated ion flux is drawn forward, counter to this gentle outflow of curtain gas, by an appropriate attractive potential on the orifice plate 10, until these ions are caught up by the portion of the curtain gas flowing through the orifice 42 of the orifice plate and hence are carried into the vacuum section.

Figure 4:
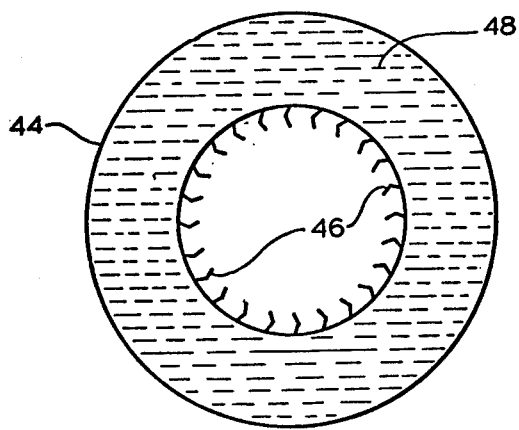
FIG. 4 is a sectional view of the cryogenic pump of FIG. 1.

The vacuum section 6 includes (see also FIG. 4) a cooling fluid reservoir 44 having fins 46. The reservoir 44 conveniently contains liquid nitrogen 48. As the curtain gas, containing the ions of interest, expands outwardly from the orifice 42, the molecules of $CO_2$ impinge on the fins 46 and deposit there, reducing the pressure in the vacuum chamber. The fins 46 are formed with appropriate trapping surface geometry, as is well known in the art of cryopumping, to maximize the trapping and depositing of the $CO_2$ molecules. By this means, an equivalent pumping speed of hundreds of thousands of litres/sec can be achieved, so that an operating vacuum in the $10^{-5}$ to $10^{-6}$ Torr range (suitable for mass spectrometry) can be obtained with an entry orifice 42 diameter of about 0.033 cm. This size is substantially larger than the 0.002 cm maximum or smaller size orifices conventionally used, so that the ion flux into the vacuum section can be increased by this invention at least by the ratio of hole areas, typically by several hundred or more.

Once a vacuum has been established (a mild vacuum may initially be created by convenient conventional means, e.g. a small mechanical roughing pump, and then increased by cryopumping), the ions of interest entering the vacuum section 6 expand in a free jet 50 and are focussed by appropriate electrostatic ion lens elements (diagrammatically indicated at 51) into a mass analyzer 52 such as a quadrupole mass spectrometer. The mass analyser 52 analyzes the ions according to their charge-to-mass ratio and allows quantitative determination by ion counting or other appropriate conventional techniques.

After the vacuum section has run for an appreciable period of time, $CO_2$ frost will build up on the fins 46 and defrosting will be required. Sufficient fin surface should therefore be provided to permit the vacuum section to operate for a sufficient interval before defrosting. In one prototype of the invention which has been operated successfully, operation was carried on for a full week before defrosting was required, but operation for a few hours will frequently be sufficient. In addition, a small additional vacuum pump 54 can be provided to remove non-condensable impurites (such as nitrogen) from the vacuum chamber. The pump 54 conveniently may be a getter ion pump.

Figure 5:
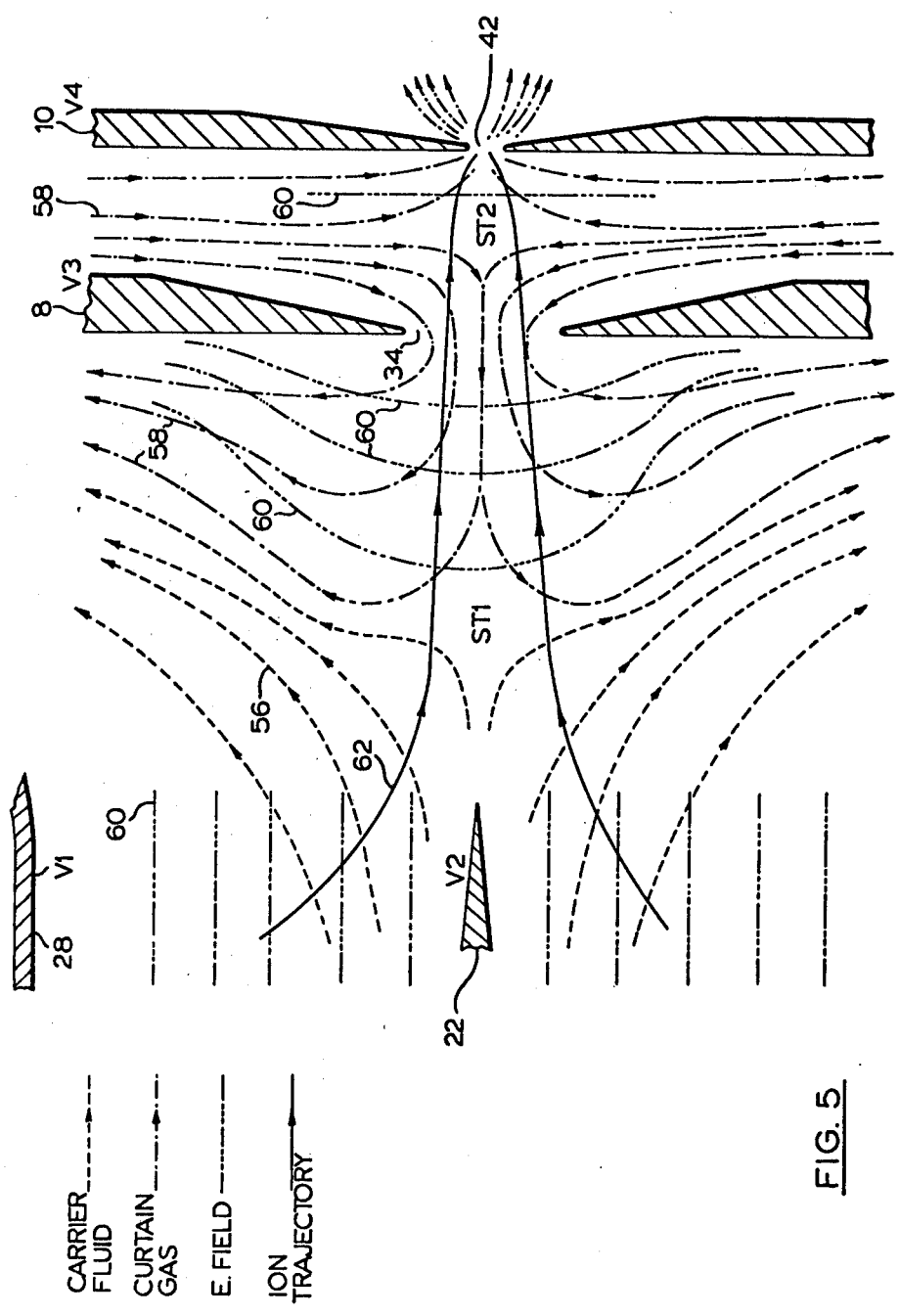
FIG. 5 is a graph showing fluid flow, electric field and ion paths.

The interaction of the crossed electric and fluid fields in the FIGS. 1 to 4 embodiment will now be described in more detail, with reference to FIG. 5. In FIG. 5, lines 56 represent the flow of the carrier fluid (which can be air), lines 58 represent the flow of the curtain gas, lines 60 are equipotential lines representing the electric field, and lines 62 represent the paths of the ions. Voltages V1, V2, V3 and V4 are applied to the electrodes 22, 28, and plates 8, 10 respectively. For analysis of positive ions, the voltages shown may all be positive, with $V1 > V2 > V3 > V4$, as indicated in Table I which follows in this description.

It will be seen from FIG. 5 that in the region between the needle 22 and the encircling electrode 28, the electric field is essentially radial and the fluid flow lines are essentially axial. Thus, assuming use of the voltages shown in Table I, as sample ions are created, the positive ions move at an angle inwardly towards the needle 22 and axially towards the interface plate 8. The negative ions are immediately separated and are drawn towards the duct wall, reducing the amount of recombination. Ideally the positive ions just miss the tip of the needle 22 and are then drawn towards the aperture 34. Preferably the trajectories of the ions in the region between the needle and the duct wall converge conically towards a point just beyond the tip of the needle at an angle in the range between 30 and 60 degrees, preferably about 45 degrees. In the region downstream of the tip of the needle 22, the radial component of the electric field is small, so that radially inward movement of the ions is slight once they move downstream of the needle tip. However, the axial electric field between the needle tip and the plate 8 is quite substantial, so that the ions are drawn at high speed relative to the local fluid velocities, towards the aperture 34.

Figure 6:
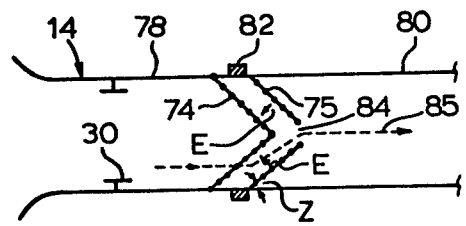
FIG. 6 is a sectional view of a modification of a portion of the FIG. 1 reaction section.
Figure 6A:
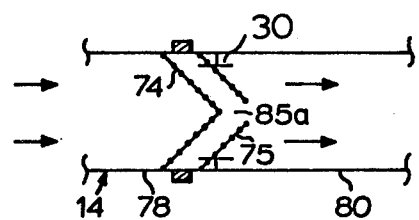
FIG. 6A is a sectional view showing a modification of the FIG. 6 apparatus.

As the carrier fluid (e.g. air) approaches the interface plate 8, it is diverted radially outwardly, as indicated by the flow lines 56. In addition the curtain gas flowing from the aperture 34 in the interface plate meets the carrier fluid, creating a stagnation point ST1. At the stagnation point ST1 (which is on the central stagnation streamline) there is no movement of fluid. However, in the region of the stagnation point ST1, the axial electric field is sufficiently high to cause the ions to move forward through the stagnation point ST1, through the counterflowing curtain gas, and through the aperture 34.

When the ions enter the space between the interface plate 8 and the orifice plate 10, they encounter a second stagnation point ST2, created by the division of the curtain gas as it divides to pass through aperture 34 and orifice 42. The axial electric field carries the ions through stagnation point ST2 and they then pass through the orifice 42. It will be noted that because the carrier fluid does not pass through either aperture 34 or orifice 42, any materials in the carrier fluid that might normally tend to clog an orifice will not have that result in the embodiment here described.

It will be appreciated from the above discussion that the downstream tip of the needle 22 should be located upstream of the stagnation point ST1. If the tip of the needle 22 were located at or beyond the stagnation point ST1, then the fluid velocity at the tip of the needle would have no axial component or would be reversed, and the desired sample ions would all be drawn onto the needle 22 (rather than just missing the tip of the needle) and would be lost. Locating the downstream tip of the needle 22 upstream of stagnation point ST1 ensures that a number of ions will be carried forward through the stagnation point. Typically the spacing between the needle tip and the interface plate 8 is between about 3 and 8 cm, while the spacing between point ST1 and the interface plate 8 is about one or two cm.

In addition, it will be seen that when the ions enter the space between plates 8, 10, they then curve towards the orifice 42. The curved ion paths are caused by the flow of curtain gas into the orifice 42 and the superimposed electric field. To achieve this curved path effect, the voltages should be adjusted so that the speed of the ions due to the electric field as they pass through the space between the plates 8, 10 is not too high; otherwise the radius of the stream tube of ions drawn through the orifice 42 is unnecessarily reduced.

The embodiment described is capable of producing ion separation as well as ion concentration. In other words, if the ion creation process creates ions A and B, ions B being unwanted, it is possible to select fluid flow and electric field parameters that A/B in the stream entering aperture 34 is greater than A/B in the ion creation region. In one test made with apparatus of the invention, with ions A and B having masses of 18 and 182 a.m.u. (atomic mass units) respectively, a separation of 5.3 was obtained (i.e. A/B at aperture 34 was 5.3 times A/B in the ion creation region). The separation occurs since ions of different masses follow different trajectories, so that ions to be removed can in substantial numbers be directed onto the needle 22 or made to miss the aperture 34.

Various modifications may be made in the FIGS. 1 to 4 arrangement. With reference to the reaction section 2, other geometries may be used to provide an electric field having a component oriented transversely to the direction of fluid flow, to concentrate the desired ions away from the duct walls and in a region in which they will be carried forward by the fluid flow. For example, and as shown in FIG. 6, electrified screens or grids 74, 75 may be employed to create the necessary transverse electric field. The direction of the field produced by such screens is indicated by arrows E. The field is generally conical to produce convergence of the desired species. When the screens are used, each screen 74, 75 is preferably cone shaped, with screen 74 being electrically connected to duct portion 78 and screen 75 being electrically connected to duct portion 80. The duct portions 78, 80 are electrically insulated from each other by a short insulating portion 82, and the duct portion 80 is electrically separate from the interface plate 8 (not shown in FIG. 5). Thus, duct portion 78 and screen 74 may be held at one potential, duct portion 80 and screen 75 at another potential, and interface plate 8 may be held at a third potential.

Each screen 74, 75 is of very fine wire, and the downstream screen 75 typically has a hole 84 at its apex to facilitate passage of ions therethrough. The spacing between the screens, and the angles formed by the cones of the screens, may be adjusted to provide the desired ion trajectories. The wire used for the screens should be as fine as possible to minimize interference with the flow of the carrier fluid.

For the FIG. 6 embodiment of the invention, a typical apparatus made according to the invention used 45 degree cones for the screens 74, 75 (i.e. the angle Z between each cone and the duct was 45 degrees). The wire used for the screens was 0.1 mm in diameter, with mesh openings each being approximately 4 mm square, clear space. The screens were located 1 cm apart, measured normal to the surface of the cones. The above dimensions are illustrative only, but it will be appreciated that for good pre-separation to occur in the FIG. 6 embodiment, the screens 74, 75 should be fairly close together. The reason for this may be seen by observing the path 85 of a typical desired ion in the FIG. 6 apparatus. The path 85 has a portion located between the two cones. Different ions will have different paths between the cones, and if it is desired to select ions which travel parallel to the cones while they are between the cones, and to eliminate ions which have a more slanting path between the cones (in order to achieve a pre-separation), then the cones should be relatively closely spaced. As shown in FIG. 6A, the ring 30 may be placed to provide an ion creation region 85A between the screens 74, 75. This reduces the loss of ions due to screen 74. Other means (for example a single screen and appropriate potentials on the duct portions) may alternatively be used to create a generally conical E field.

The foregoing description has dealt with an embodiment of the invention which is suited for analyzing samples which are available in large quantities but in which the trace gases to be analyzed are present in very minute proportions. In some cases, the trace gas to be analyzed will be limited in quantity and may appear as a discrete region of higher concentration in a carrier gas. The trace gas and its carrier gas may emerge (see FIG. 7) for example from the tip of the outlet tube 86 connected to a gas chromatograph (not shown). A reagent gas, for example air, nitrogen, air with butane or methylamine or ozone, is introduced via inlet 12 into duct 14 at a flow which is approximately equal to the flow from tube 86. The flow velocities are adjusted to obtain the desired trajectories as before. Ionization is achieved as before by a tritium foil 88 located in the duct 14 surrounding the tube 86. The tritium foil creates reactant ions in the reagent gas. The reactant ions are focussed onto the central region and react with the trace gas to form product ions in the central region. A transverse electric field may be achieved as before by electrifying both the central tube 86 (which thus serves as the central electrode) and the surrounding duct 14, in order to concentrate the flux of the reactant ions onto the central region ions so that they may react with the trace gas. The ion flow in the central region will then pass through the aperture 34 in the interface plate 8.

Figure 7:
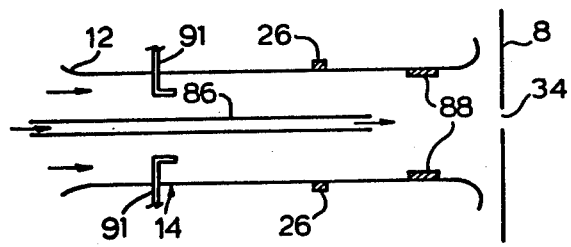
FIG. 7 is a sectional view showing a modification of the FIG. 1 reaction section.
Figure 7A:
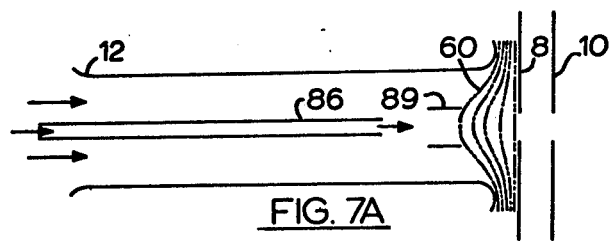
FIG. 7A and 7B are sectional views showing further modifications of the FIG. 1 reaction section.

A modification of the FIG. 7 apparatus is shown in FIG. 7A, where corresponding reference numerals indicate corresponding parts. In FIG. 7A the tritium foil 88 has been replaced by a tritium foil 89 of relatively small diameter encircling the stream of gas emerging from tube 86. Foil 89 is suspended by means not shown and is connected to a source of potential, as are interface plate 8 and orifice plate 10, to create electric field lines as shown at 60 in FIG. 7A. Typical potentials for negative ion operation are: foil 89, −2000 volts; plate 8, −200 volts; and plate 10, −130 volts. The small ring 89 provides efficient use of the beta rays for creating ions, and the field 60 directs the ions through the aperture 34. Tests have shown the FIG. 7A arrangement of ring and field to be quite effective in producing ions and in directing them through aperture 34.

Figure 7B:
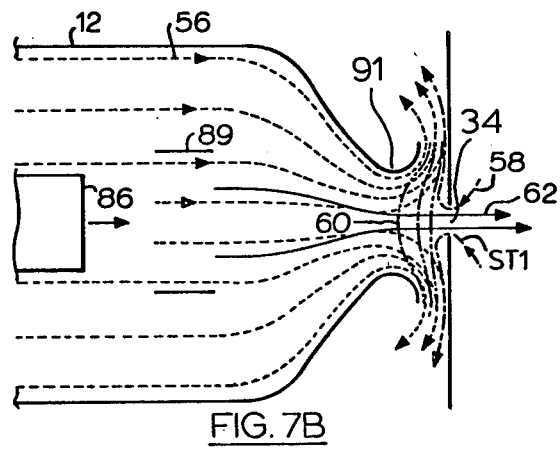
Figure 8:
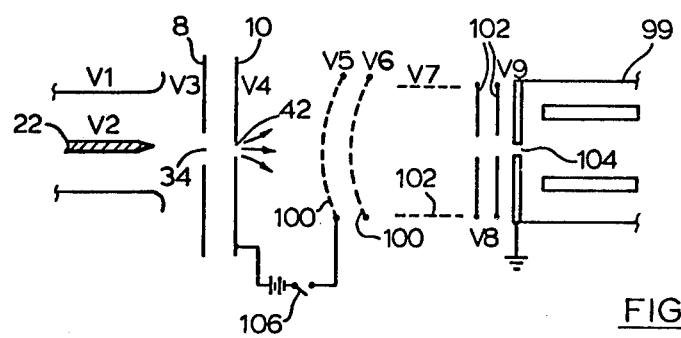
FIG. 8 is a diagrammatic view showing typical potentials applied to the FIG. 1 apparatus.

Reference is next made to FIG. 7B, which shows a modification of the FIG. 7A apparatus. In FIG. 7B, the duct 12 narrows smoothly in diameter adjacent the interface plate 8, as indicated at 91 in FIG. 7B. The carrier fluid (e.g. air) in the duct 12 follows a path as indicated by streamlines 56. It will be seen that the streamlines 56 have all contracted, giving a form of concentration. When the carrier fluid approaches the interface plate 8, the streamlines 56 spread out again. However, the electric field at the aperture 34 (indicated by lines 60) is made strong enough to prevent the reduced diameter stream tube of ions (whose path is indicated by lines 62) from spreading out appreciably. For this purpose the field strength is adjusted so that the ion drift velocity is typically at least 3 to 5 times the local fluid velocity, although these values may vary depending on the parameters of the system. The result is that the narrow stream tube of ions is funnelled through the aperture 34.

The stagnation point ST1 upstream of the aperture plate 8 in the FIG. 7B embodiment is very close to the aperture plate 8. It will be seen from FIG. 7B that the electric field (produced by potentials on plate 8 and in the walls of duct 12) is such that there is a component of the field transverse to the direction of gas flow, at a location upstream from stagnation point ST1.

The above described contraction of the stream tube containing the ions can substantially increase the ion signal transmitted into the vacuum chamber. For example, a 10 to 1 reduction in the diameter of the ion stream tube will result in a 100 times increase in the number of ions per unit area. It will be understood that the contours of the reduced diameter portion 91 of duct 12 should be designed so that laminar flow is preserved; this form of design is well known to those skilled in the art. Allowance will also be made for the effusion of curtain gas 58 from the aperture 34, in the design of the narrowed portion 91.

The concentration method shown in FIG. 7B may be used not only with the FIG. 7 or 7A apparatus, but also with the FIG. 1 apparatus, since the stream tube of ions leaving the needle 22 can still benefit from a reduction in diameter. It may also be used with the FIG. 1 apparatus with the needle 22 completely removed and with the ring 30 reduced in diameter and made like the ring 89 of FIG. 7A, or it may be used in the FIG. 6 apparatus, with the conical screens 74, 75 or with these screens replaced by a ring such as ring 88 of FIG. 7.

If desired, other reactive media such as butane gas, nitric oxide, methylamine, ozone, etc. may also be introduced into the carrier gas of the FIG. 1 apparatus or in the other apparatus described, to modify the ion molecule reactions to increase the sensitivity of the apparatus for desired species. Such reactive media may be added for example via inlet ducts 90 shown in FIG. 1 or inlet ducts 91 shown in FIG. 7.

In a typical device made in accordance with the invention, and using a quadrupole mass spectrometer 99, (FIG. 68), curved focussing screens 100 may be used, together with electrostatic lens elements 102, to focus the ions through the inlet aperture 104 in the casing of the spectrometer 99. Typical potentials used in equipment made according to the invention are shown in Table I below. All potentials shown are referenced to ground and were used for collection of positive ions.

TABLE I

| | | |
|---|---|---|
| V1 : | + 2800 to + 3600 | V6 : − 90 |
| V2 : | + 1400 to + 2000 | V7 : − 90 |
| V3 : | + 50 to + 1500 | V8 : − 90 |
| V4 : | 0 to + 120 | V9 : − 120 |
| V5 : | 0 | |

It will be noted that with the apparatus of the invention, the ions to be analyzed are formed gently, for example by simple transference of charge to them, rather than being impacted with electrons. Therefore, the number of fragments to be analyzed is much reduced as compared with typical conventional mass spectrometer. However, if desired, a field can be applied to the ions within the vacuum chamber in order to accelerate them in regions in which the cryogas density is sufficiently high to permit energetic ion molecule collisions which will fragment the ions. For example, a one hundred volt potential difference may be applied between the orifice plate 10 and the first screen 100 to accelerate and fragment ions. A simple switch 106 may be employed to switch the accelerating voltage on or off, so that either the intact ions, or their fragments, may be analyzed in the mass spectrometer 99. This flexibility may be combined with the added capability of positive and negative mode analysis, by providing another switch (not shown) to apply voltages appropriate for analysis of negative ions. Thus the operating mode of the apparatus may readily be switched.

Figure 9:
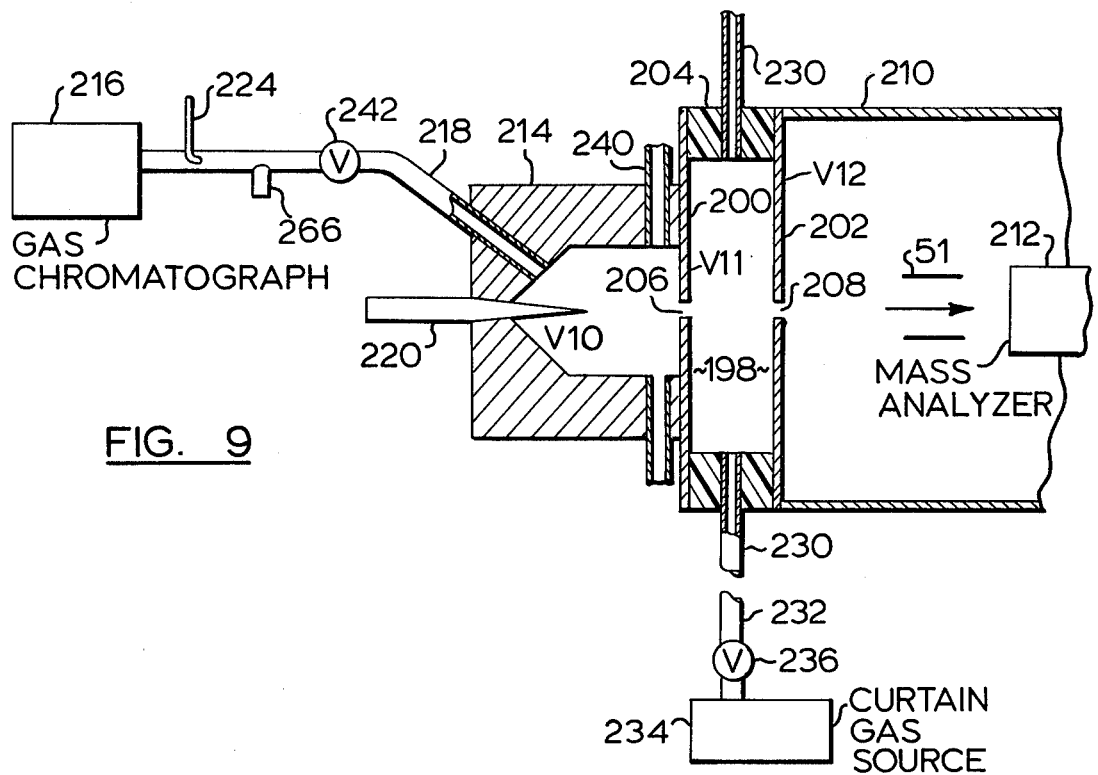
FIG. 9 is a sectional view of another embodiment of the invention.

Reference is next made to FIG. 9, which shows a further embodiment of the invention. FIG. 9 shows a curtain gas chamber 198 defined by a metal interface plate 200 and a metal orifice plate 202 which are spaced apart by an annular insulator 204. Plates 200, 202 contain an aligned aperture 206 and orifice 208 respectively. Plate 202 forms one end of a vacuum chamber 210 containing mass analyzer 212, while plate 200 forms one end of an ionization or reaction chamber 214. The vacuum chamber 210 is pumped by any appropriate means.

The sample gas containing the trace components of interest (either atoms or molecules) is supplied from a source 216 through a conduit 218 into the chamber 214. An electric discharge needle 220 is located in the wall of chamber 214 opposite the interface plate 200, in the path of flow from conduit 218, and is axially aligned with the apertures 206, 208. Electric potentials of appropriate strength and sign are applied to the needle 220 and to the plates 200, 202 to induce ionization between the tip of the needle 220 and the interface plate 200. The electric field lines between these elements are indicated by lines 222 (the same line coding is used as in FIGS. 5, 7A and 7B).

In operation the trace components may be ionized directly by the discharge from the needle 220 or by other discharge process (e.g. heat, an RF field, etc). Alternatively the ionization process for the trace components may be indirect, through the sequence of steps in the chemical ionization process. In the latter case one or more chemical reagent gases may if desired be added to the sample flow via conduit 224 which leads into conduit 218. Desired ion-molecule reactions then proceed in the chamber 224, with the ion products which are produced dependent upon the gas mixture which is supplied.

A further method of producing a sample gas is as follows. The trace material to be analyzed may be dissolved in a solvent. For example, air containing the trace material may be bubbled through the solvent. If the trace material is in water, than the water itself may be the solvent. Alternatively, the trace may be collected on a solid substrate, e.g. charcoal, and then transferred to a solvent (e.g. benzene) by shaking the substrate in the solvent. The solvent may be benzene, methylene chloride, hexane, isooctane, or any other appropriate solvent.

The solvent, with the trace material therein, is then vaporized. This may be performed by injecting it into a stream of warm carrier gas. If a chemical ionization process is desired, then the solvent may be used as a chemical ionization reagent, or an additonal reagent can be added as part of or can be the entire carrier gas.

The trace components may also be emitted from a liquid chromatograph. In this case the liquid carrier will be vaporized before ionization.

Curtain gas is provided in the FIG. 9 embodiment by inlet ducts 230 arranged to create a generally circular flow pattern having a circumferential component but directed radially inwardly. Any other means may be used to create a similar circular flow pattern. The curtain gas is provided via a feed conduit 232 from a curtain gas source 234. A valve 236 in the conduit 232 permits control of the pressure in the curtain gas chamber 198.

The FIG. 9 embodiment may be operated with the flow of curtain gas less than, equal to, or more than sufficient to match the flow through the orifice 208 into the vacuum chamber 210. Each one of these conditions has specific advantages. However, regardless of the flow, the electric field in the chamber 214, caused by the voltages applied to needle 220 and plate 202, and continued in the same direction by a third voltage on plate 204, is arranged so that the ions are drifted, at velocities higher than the gas flows, out of the chamber 214, across the curtain gas in curtain gas chamber 198, and on into the vacuum chamber 210. Typical voltages and dimensions which may be used in the FIG. 9 embodiment are given in Table II at the end of this description. Excess gas in the chamber 214 escapes or is pumped out via vents 240 in the outer wall of chamber 214 adjacent the interface plate 200.

When the curtain gas flow through the curtain gas feed conduit 232 matches or slightly exceeds the flow from curtain gas chamber 198 out through the orifice 208, then the flow of sample gas from chamber 214 into vacuum is blocked but ions are transmitted. This is the mode in which the FIG. 1 apparatus is operated. The gas curtain then has the following advantages.

Firstly, the rate of flow of sample gas is independent of the flow rate into vacuum. Different sources of sample flows, for example capillary column gas chromatographs, packed column gas chromatographs, direct air samples, samples desorbed from a collector trap into a sample carrier gas, all have their own appropriate best gas flows which can now be accomodated without changing or matching the orifice 208 for various sample inlet systems.

Secondly, any sample gas can be used, cryopumpable or non-cryopumpable (such as helium), moisture laden or particle laden (such as normal air), and at almost any temperature. The curtain gas ensures that the orifice 208 will not become plugged with particulates, and because the curtain gas can be ultra-pure and dry and at an independently controlled temperature, problems of unwanted non-equilibrium clustering can be reduced. Non-equilibrium clustering is a reaction which occurs in the adiabatic free jet expansion in the vacuum chamber, due to the cooling effect during the expansion. Since the molecules which cluster most severely around the trace gas ions are usually water molecules and other impurities, the non-equilibrium clustering can be drastically reduced by the use of a pure curtain gas.

Thirdly, the independence of the flow rate of the sample gas from the flow rate into vacuum can permit increased sensitivity when only a minute amount of sample gas is available (e.g. from a small sample gas container or trap) and when the desired chemical reaction rate constants related to the ionization of the trace components are low. For example, the well known techniques of stop-column chromatography may be used, in which the flow of gas through the gas chromatograph is stopped for a desired interval while analysis is carried out on a given sample. Similarly, in the present invention, the gas flows may be adjusted to hold the sample gas in the chamber 214 for a longer period of time when entry of the desired trace components into the chamber 214 is detected. The entry of the desired trace components into the chamber 214 may be detected by the mass analyzer 212, since the output signal from the analyzer 212 will then begin to increase. A valve 242 may be provided in the conduit 218 to stop or reduce the flow of sample gas at this time, to permit the sample to be more fully ionized. If the pressure in the reaction chamber 214 falls due to the reduced sample gas flow, the flow of curtain gas may also be reduced at this time by valve 236, to maintain just sufficient curtain gas to prevent the sample gas from entering the curtain gas chamber 198, but to avoid rapid flushing of the reaction chamber 214 with curtain gas.

Figure 10:
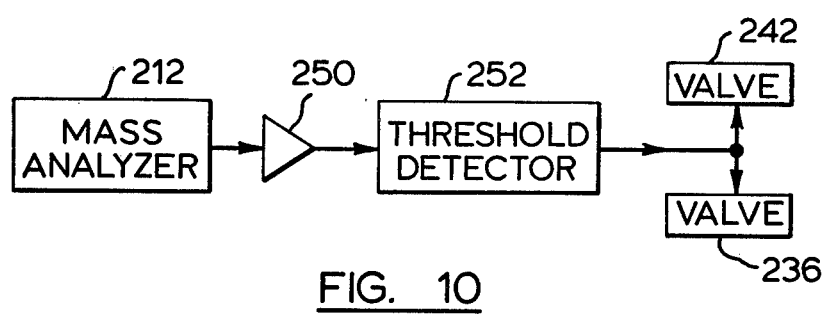
FIG. 10 is a block diagram of a control system for the FIG. 9 embodiment.

If desired, and as shown in FIG. 10, the increased output signal from the mass analyzer 212 when the desired trace components arrive in reaction chamber 214, may be amplified by an amplifier 250, the output of which is used to operate a threshold detector 252. When the signal at detector 252 rises above its preset trigger level for a period of time which is set sufficiently long to reduce the effect of transients, the detector 252 operates and adjusts valves 236, 242 (which may be solenoid valves) to preset conditions in which they control the gas flows to retain the current sample in the reaction chamber 214 for as long as possible. The valves 236, 242 may be reset to their normal conditions either manually or automatically, when the output of amplifier 250 falls below the threshold level of detector 252.

If desired, after the sample of interest has been stopped and analyzed, the reaction chamber 214 may be flushed out by increasing the curtain gas flow substantially for a short period of time.

A further advantage of the gas curtain is that the curtain gas may be an appropriate cryopumpable gas, so that the advantages of cryopumping may be used even though the sample gas itself may not itself be readily cryopumpable. This feature is referred to in more detail in our said copending application.

Figure 11:
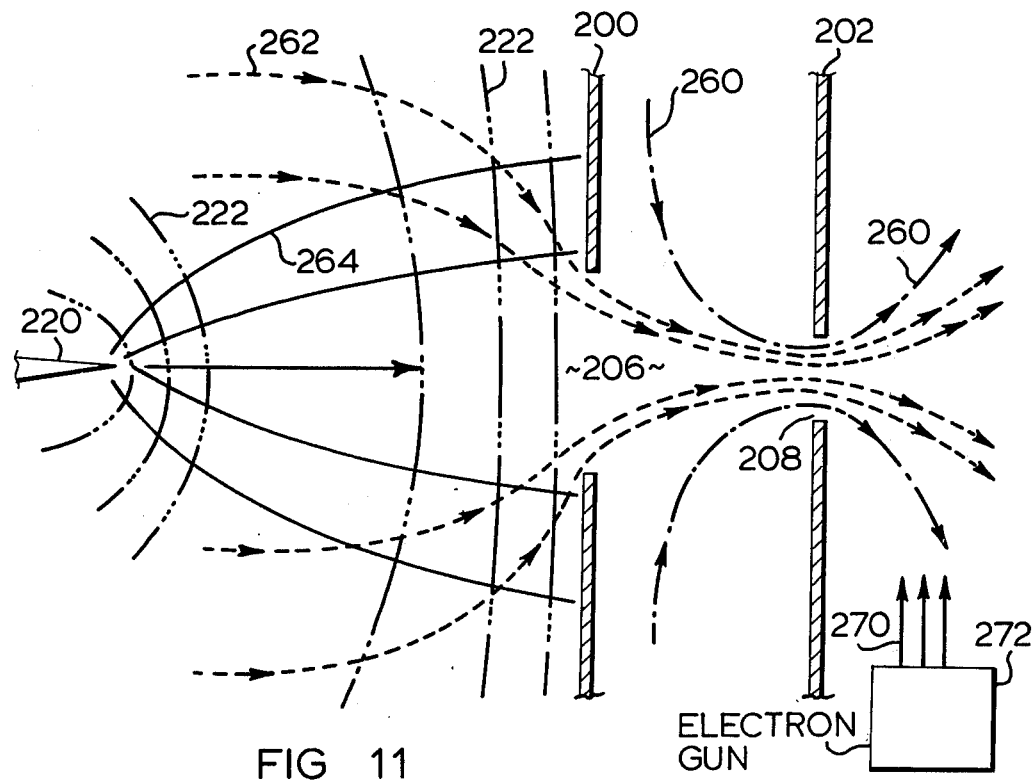
FIG. 11 is a view similar to FIG. 10 and showing another mode of operation of the FIG. 10 system.

A second mode of operation of the FIG. 9 apparatus may be termed a "pierced curtain." In this mode the curtain gas inflow is insufficient to match the required flow into the vacuum chamber 210 through the orifice 208, the difference being made up by the sample gas flow. The curtain gas flow may then be controlled to yield, in effect, an infinitely variable orifice for the sample gas while retaining the maximum fixed open orifice as a window for ions. This situation is illustrated in FIG. 11, in which the electric field lines are shown at 222, the curtain gas flow is indicated at 260, the sample gas flow at 262, and the ion flux is shown at 264.

It will be seen that the curtain gas flow, because it occurs radially inwardly towards the axis of the aligned orifice 208 and aperture 206, encircles or sheaths the sample flow into the vacuum chamber. As the curtain gas flow, indicated by lines 260, increases, it increasingly constricts the sample gas flow 262 towards the centre line or axis of the orifice 208 and aperture 206. This reduces the sample flow to such an extent as may be desired. Excess sample gas if any is discharged from vents 240.

In operation, the curtain gas flow may be controlled by monitoring the pressure in the sample gas conduit 218, by means of pressure transducer and indicator 266, and then adjusting the curtain gas flow with valve 236 to admit the desired amount of sample flow into the vacuum chamber 210. The sample flow admitted can be varied from the full sample flow (if the vacuum pumping capability is high enough) down to zero, in an infinitely variable manner. Again, the orifice 208 may be as large as the available vacuum pumping equipment permits, and again cryopumping is advantageous.

One of the advantages of the variable orifice mode of operation is that the effective variable orifice permits various desired sample flows to be matched conveniently to the flow into the vacuum. For example, a large orifice 208 may pass a larger flow than desirable for optimum operation of a capillary column gas chromatograph, thus pulling the column pressure sub-atmospheric and degrading its operation. Sufficient supplementary curtain gas flow can be provided to eliminate this problem. If desired, the signal from pressure transducer and indicator 266 can be used to control the valve 236 to maintain the pressure in conduit 218 at the desired pressure.

The flow matching capability referred to above was also present in the previously described ion window mode of operation, where the excess curtain gas flow plus the sample gas were discharged through vents 240, but in the variable orifice mode of operation the flow matching capability includes the following further advantages.

Firstly, it will be seen that the ion flux lines 264 are arranged orthogonal to the electric field lines 222 in FIG. 11. Thus, only that portion of the ion flux 264 which passes through the aperture 206 can contribute to the desired ion signal. Ions outside aperture 206 are incident on the metal plate 200 producing the field, where they are neutralized, and are re-emitted promptly as molecules if the source temperature is high enough. In the first mode, i.e. the ion window mode, these molecules will be swept out the vents 240. In the variable orifice mode, they are carried forward by the sample gas stream lines 262 and must pass through the central region where they have an opportunity to participate in the ion-molecule reactions again and to become re-ionized by contact with reagent ions. The re-ionized trace molecules again thus contribute to the ion signal, increasing the total ion signal count.

A further advantage of the pierced curtain mode is that the surrounding curtain gas constrains the sample during the gas dynamic expansion immediately downstream of the orifice 208. This keeps the trace ions closer to the centre line or axis of the orifice 208, facilitating their focusing into the mass analyzer 212 while the surrounding gases are stripped away and removed.

If substantially all of the sample gas flow is admitted into the vacuum chamber 210, then the ionizing means may be located in the vacuum chamber 210 rather than in the chamber 214, and the electric fields caused by the potentials on needle 220 and plates 200, 202 may be removed. Instead, an ionizing flux may be provided in the vacuum chamber 210 by convenient means such as a high perveance magnetically collimated electron gun 270, which directs a stream of electrons indicated at 272 towards the stream emerging from the orifice 208 to create trace ions in the vacuum chamber by electron impact. Because of the constraining effect of the curtain gas, which limits the expansion of the sample gas in the region immediately downstream of the orifice 208, the resultant sample ions will be created in a region in space more restricted towards the centre line of the apparatus, resulting in more efficient focusing of the ions into the mass analyzer 212.

Although the curtain gas need not necessarily be cryopumpable, it is preferred that it be cryopumpable. Cryopumping the curtain gas permits increased pumping speeds with apparatus which is much smaller, lighter, and less costly than apparatus having conventional vacuum pumping systems having equivalent pumping speeds.

Typical cryopumpable curtain gases which may be used, depending on the temperature to which the vacuum chamber fins are cooled, are nitrogen, argon, carbon dioxide, oxygen (the latter for use with positive ions only), and appropriate freon gases. All will have a vapour pressure substantially less than atmospheric (typically $10^{-4}$ torr or less) at a temperature to which the walls of the vacuum chamber can be conveniently cooled.

In addition, the sample gas itself may be cryopumpable. Such gas may be a cryopumpable chemical reagent gas such as water vapour, isobutane, propane, benzene, methylene chloride, hexane, isooctane, or other appropriate reagent. The sample gas may also be a gas such as nitrogen or argon. In that event, even when the sample gas is admitted to the vacuum chamber, cryopumping may still be used.

TABLE II

| | |
|---|---|
| V10: | +1000 to +3000 volts |
| V11: | +50 to +300 volts |
| V12: | +2 to +20 volts |

The above voltages are for positive ion production and transfer. The sign of the voltages will be reversed for negative ions.

What we claim is:

1. A method of analyzing trace components in a vacuum chamber, comprising:
   (a) selecting a curtain gas of low reactivity with said trace components,
   (b) directing said curtain gas into a curtain gas chamber adjacent said vacuum chamber, said curtain gas chamber communicating with said vacuum chamber through an orifice therebetween,
   (c) maintaining a vacuum in said vacuum chamber so that some of said curtain gas in said curtain gas chamber will pass through said orifice into said vacuum chamber and will then expand in said vacuum chamber about the axis of said orifice,
   (d) supplying a sample gas at a selected flow to a sample gas region adjacent said curtain gas chamber, said sample gas containing said trace components to be analyzed, said sample gas region communicating with said curtain gas chamber through an opening therebetween and said sample gas region having vent means therein,
   (e) controlling the flow of said curtain gas to said curtain gas chamber so that the pressure in said certain gas chamber is greater than the pressure in said sample gas region for said curtain gas to prevent entry of said sample gas into said curtain gas chamber and so that any said curtain gas entering said curtain gas chamber in excess of that flowing through said orifice will flow from said curtain gas chamber through said opening into said sample gas region,
   (f) removing said sample gas and said excess curtain gas from said sample gas region through said vent means,
   (g) ionizing at least some of said trace components in said sample gas region, thereby forming trace ions in said sample gas region,
   (h) creating an electric field in said sample gas region and in said curtain gas chamber to draw said trace ions from said sample gas region through said opening, through said curtain gas chamber, and through said orifice into said vacuum chamber, so that said curtain gas functions to prevent said sample gas from entering said vacuum chamber and also at the same time functions as an ion window to permit ions to pass therethrough under the influence of said electric field,
   (i) directing said ions in said vacuum chamber along a path directed away from said expanding curtain gas therein and into an analyzer located in vacuum in said vacuum chamber,
   (j) and analyzing said ions in said analyzer.

2. A method according to claim 1 and including the step of monitoring the pressure of said sample gas in said sample gas region and controlling the flow of said curtain gas into said curtain gas chamber to provide a controlled flow of said curtain gas through said opening into said sample gas region to maintain the pressure of said sample gas in said sample gas region at a predetermined pressure.

3. A method according to claim 1 wherein said sample gas region communicates with the outlet of a sample gas producing device and including the step of monitoring the pressure of said sample gas in said sample gas region and controlling the flow of said curtain gas into said curtain gas chamber to provide sufficient flow of said curtain gas through said opening into said sample gas region to prevent the pressure in said device being being drawn below atmospheric pressure.

4. A method according to claim 1 and including the step of supplying said sample gas from a source of limited volume, so that said sample gas is limited in quantity, and reducing the net flow of said sample gas into said sample gas region for a selected interval to hold said trace gas molecules in said sample gas region for an increased period of time, thereby to increase the number of trace gas molecules which are ionized.

5. A method according to claim 1 and including the step of substantially increasing the flow of said curtain gas into said curtain gas chamber for a selected period of time to create a substantial flow of said curtain gas from said curtain gas chamber through said opening into said sample gas region to flush out said sample gas region with curtain gas.

6. A method of analyzing trace components in a vacuum chamber, comprising:
   (a) selecting a curtain gas of low reactivity with said trace components,
   (b) directing a flow of said curtain gas into a curtain gas chamber adjacent said vacuum chamber, said curtain gas chamber communicating with said vacuum chamber through an orifice therebetween,
   (c) maintaining a vacuum in said vacuum chamber so that said curtain gas in said curtain gas chamber will pass through said orifice into said vacuum chamber and will then expand in said vacuum chamber about the axis of said orifice,
   (d) supplying a sample gas at a selected flow to a sample gas region adjacent said gas curtain chamber, said sample gas containing said trace components to be analyzed, said sample gas region communicating with said gas curtain chamber through an opening therebetween, so that some of said sample gas will tend to flow through said opening into said gas curtain chamber and through said orifice into said vacuum chamber, said opening and said orifice being substantially aligned along said axis, (e) controlling the flow of said curtain gas to said curtain gas chamber so that such flow is less than the total flow of gas from said curtain gas chamber through said orifice into said vacuum chamber thus to admit a controlled limited flow of said sample gas from said sample gas region in a stream along said axis through said opening, through said curtain gas chamber, and through said orifice into said vacuum chamber, (f) directing said curtain gas in said curtain gas chamber in a flow pattern generally encircling said axis and directed radially inwardly toward said axis, and providing a flow of said curtain gas in said pattern sufficient so that said curtain gas encircles and constrains the diameter of said stream of sample gas flowing through said curtain gas chamber and through said orifice, (g) ionizing at least some of said trace components in said sample gas, (h) directing said ions in said vacuum chamber along a path directed away from said expanding curtain gas therein and into an analyzer located in vacuum in said vacuum chamber, (i) and analyzing said ions in said analyzer.

7. A method of analyzing trace components in a vacuum chamber, comprising:

(a) selecting a curtain gas of low reactivity with said trace components, (b) directing said curtain gas into a curtain gas chamber adjacent said vacuum chamber, said curtain gas chamber communicating with said vacuum chamber through an orifice therebetween, (c) maintaining a vacuum in said vacuum chamber so that said curtain gas in said curtain gas chamber will pass through said orifice into said vacuum chamber and will then expand in said vacuum chamber about the axis of said orifice, (d) supplying a sample gas at a selected flow to a sample gas region adjacent said curtain gas chamber, said sample gas containing said trace components to be analyzed, said sample gas region communicating with said curtain gas chamber through an opening therebetween, so that some of said sample gas will tend to flow through said opening into said curtain gas chamber and through said orifice into said vacuum chamber, (e) controlling the flow of said curtain gas to said curtain gas chamber so that such flow is less than the total flow of gas from said curtain gas chamber through said orifice into said vacuum chamber thus to admit a controlled flow of said sample gas from said sample gas region through said opening, through said curtain gas chamber, and through said orifice into said vacuum chamber, (f) ionizing at least some of said trace components in said sample gas region, thereby forming trace ions in said sample gas region, (g) creating an electric field in said sample gas region and in said curtain gas chamber to draw said trace ions from said sample gas region through said opening, through said curtain gas chamber, and through said orifice into said vacuum chamber, so that said curtain gas functions as a controllable orifice to control the amount of said sample gas entering said vacuum chamber and also at the same time functions as an ion window to permit ions to pass therethrough under the influence of said electric field, (i) directing said ions in said vacuum chamber along a path directed away from said expanding curtain gas therein and into an analyzer located in vacuum in said vacuum chamber, (j) and analyzing said ions in said analyzer.

8. A method according to claim 7 wherein said opening and orifice are substantially aligned along said axis so that said sample gas tends to travel through said opening, through said curtain gas chamber and through said orifice in a stream directed along said axis, and including the step of directing said curtain gas in said curtain gas chamber in a flow pattern generally encircling said axis and directed radially inwardly toward said axis, and providing a flow of said curtain gas in said pattern sufficient so that said curtain gas encircles and constrains the diameter of said stream of said sample gas flowing through said curtain gas chamber.

9. A method according to claim 7 wherein said opening and orifice are substantially aligned along an axis so that said sample gas tends to travel through said opening, through said curtain gas chamber and through said orifice in a stream directed along said axis, and including the step of directing said curtain gas in said curtain gas chamber in a flow pattern generally encircling said axis and directed radially inwardly toward said axis, and providing a flow of said gas in said pattern sufficient so that said curtain gas encircles said stream of sample gas flowing through said orifice and constrains the expansion of said sample gas immediately downstream of said orifice in said vacuum chamber.

10. A method according to claim 7 wherein said sample gas region communicates with the outlet of a sample gas producing device and including the step of monitoring the pressure of said sample gas in said sample gas region and providing a sufficient flow of said curtain gas into said curtain gas chamber to provide sufficient flow of said curtain gas through said opening into said sample gas region to prevent the pressure in said device from being drawn below atmospheric pressure.

11. A method according to claim 7 and including the step of supplying said sample gas from a source of limited volume, so that said sample gas is limited in quantity, and increasing the flow of said curtain gas into said current gas chamber for a selected interval to restrict flow of said sample gas from said sample gas region into said curtain gas chamber thus to hold said trace gas molecules in said sample gas region for an increased period of time, thereby to increase the number of trace gas molecules which are ionized.

12. A method according to claim 7 wherein said sample gas region has a vent therein and including the step of substantially increasing the flow of said curtain gas into said curtain gas chamber for a selected period of time to create a substantial flow of said curtain gas from said curtain gas chamber through said orifice into said sample gas region to flush out said sample gas region with curtain gas.

13. A method according to claim 7 and including the step of selecting a curtain gas and a sample gas both of which, when deposited in solid phase at a predetermined temperature, have vapour pressures substantially less than atmospheric, and further including the step of cooling at least a portion of the interior surface of said vacuum chamber to below said predetermined temperature, whereby to condense said curtain gas and said sample gas on said portion of said interior surface.

* * * * *